(12) United States Patent
Gluckman et al.

(10) Patent No.: US 6,204,240 B1
(45) Date of Patent: Mar. 20, 2001

(54) TGF-β1 TO IMPROVE NEURAL OUTCOME (75) Inventors: Peter Gluckman, Remeura (NZ); Karoly Nikolics, Belmont, CA (US); Christopher Williams, Graton (NZ)

(73) Assignee: Genentech, Inc., S. San Francisco, CA (US)

(*) Notice: Subject to any disclaimer, the term of this patent is extended or adjusted under 35 U.S.C. 154(b) by 0 days.

(21) Appl. No.: 08/232,118

(22) PCT Filed: Nov. 20, 1992

(86) PCT No.: PCT/US92/09974

§ 371 Date: May 2, 1994

§ 102(e) Date: May 2, 1994

(87) PCT Pub. No.: WO91/02067

PCT Pub. Date: Feb. 21, 1991

(30) Foreign Application Priority Data

Nov. 22, 1991 (NZ) ...................................................... 240696

(51) Int. Cl.[7] .......................... A61K 38/18; A61K 38/19
(52) U.S. Cl. .................................................. 514/2; 514/12
(58) Field of Search ......................... 514/2, 12; 530/303, 530/350, 351

(56) References Cited

U.S. PATENT DOCUMENTS

| 4,886,747 | 12/1989 | Derynck et al. . |
| 5,093,317 | * 3/1992 | Lewis et al. . |
| 5,104,977 | 4/1992 | Sporn et al. . |
| 5,182,111 | * 1/1993 | Aebischer et al. . |
| 5,262,319 | 11/1993 | Iwata et al. . |

FOREIGN PATENT DOCUMENTS

| 9102067 | 2/1991 | (WO) . |
| 91/15222 | 10/1991 | (WO) . |

OTHER PUBLICATIONS

Johns et al., "Successful Treatment of Experimental Allergic Encephalomyelitis with Transforming Growth Factor–β1[1]," *The Journal of Immunology*, 147(6):1792–1796 (1991).

Sakai et al., Serum and Transforming Growth Factor β Regulate Glial Fibrillary Acidic Protein in Serum–Free–Derived Mouse Embryo Cells, *Proc. Natl. Acad. Sci., USA*, 87:8378–8382 (1990).

Ren and Flanders, "Transforming Growth Factors–β Protect Primary Rat Hippocampal Neuronal Cultures from Degeneration Induced by β–Amyloid Peptide," *Brain Research*, 732:16–24 (1996).

Gross et al., "Transforming Growth Factor–β Reduces Infarct Size After Eperimental Cerebral Ischemia in Rabbit Model," *Stroke*, 24:557–562 (1993).

Baldwin et al., "Blood–Brain Barrier Breach Following Cortical Contusion in the Rat," *J. Neurosurg.*, 85:476–481 (1996).

Belayev et al., "Quantitative Evaluation of Blood–Brain Barrier Permeability Following Middle Cerebral Artery Occlusion in Rats," *Brain Research*, 739:88–96 (1996).

Kirino, T., "Delayed Neuronal Death in the Gerbil Hippocampus Following Ischemia," *Brain Res.*, 239:57–69 (1982).

Pulsinelli et al., "Temporal Profile of Neuronal Damage in a Model of Transient Forebrain Ischemia," *Ann. Neuroal.* 11:491–498 (1982).

Pardridge, W.M., "Transnasal and Intraventricular Delivery of Drugs," In: *Peptide Drug Delivery to the Brain*, Pardridge, W.M. (Ed.), Raven Press: New York, pp. 99–122 (1991).

Assoian et al., "Transforming Growth Factor–β in Human Platelets" *J. of Biol. Chem.* 258(11):7155–7160 (Jun. 10, 1983).

de Martin et al., "Complementary DNA for human glioblastoma–derived T cell suppressor factor, a novel member of the transforming growth factor–β gene family" *EMBO Journal* 6(12):3673–3677 (1987).

Dernyck et al., "Human transforming growth factor–β complementary DNA sequence and expression in normal and transformed cells" *Nature* 316:701–705 (Aug. 22, 1985).

Derynck et al., "A new type of transforming growth factor–β, TGF–β3" *EMBO Journal* 7(12):3737–3743 (1988).

Frolik et al., "Purification and initial characterization of a type β transforming growth factor from human placenta" *Proc. Natl. Acad. Sci. USA* 80:3676–3680 (Jun. 1983).

Heimark et al., "Inhibition of Endothelial Regeneration by Type–Beta Transforming Growth Factor from Platelets" *Science* 233:1078–1080 (Sep. 5, 1986).

Jakowlow et al., "Complementary Deoxyribonucleic Acid Cloning of a Messenger Ribonucleic Acid Encoding Transforming Growth Factor–β4 from Chicken Embryo Chondrocytes" *Molecular Endocrinology* pp. 1186–1195 (1988).

Jakowlow et al., "Complementary Deoxyribonucleic Acid Cloning of a Novel Transforming Growth Factor–β Messenger Ribonucleic Acid from Chick Embryo Chondrocytes" *Molecular Endocrinology* 2(8):747–755 (1988).

(List continued on next page.)

*Primary Examiner*—Gary L. Kunz
*Assistant Examiner*—Stephen Gucker
(74) *Attorney, Agent, or Firm*—Sean Johnston; Flehr Hohbach Test Albritton & Herbert LLP (57) ABSTRACT

The invention relates to methods of treating injuries to or diseases of the central nervous system which methods involve increasing the active concentration(s) of transforming growth factor beta 1 (TGF-β1) and/or analogues thereof in the central nervous system of the patient. The present invention also provides pharmaceutical compositions comprising TGF-β1 and/or analogues thereof for administration to a patient prior to, simultaneous with, or following a neural insult, which compositions are useful in minimizing damage to the central nervous system that would otherwise occur following the insult.

6 Claims, 3 Drawing Sheets

OTHER PUBLICATIONS

Kondaiah et al., "Identification of a Novel Transforming Growth Factor–β (TGF–β5) mRNA in Xenopus Laevis" *Journal of Biological Chemistry* 265(2):1089–1093 (1990).

Madisen et al., "Transforming Growth Factor–β2: cDNA Cloning and Sequence Analysis" *DNA* 7(1):1–8 (1988).

Roberts et al., "The Transforming Growth Factor–βs" *Peptide Growth Factors and Their Receptors I*, Spriner–Verlag, Chapter 8, pp. 419–472 (1990).

Sporn et al., "Peptide growth factors are multifunctional" *Nature* 332:217–219 (1988).

Sporn et al., "Some Recent Advances in the Chemistry and Biology of Transforming Growth Factor–Beta" *Journal of Cell Biology* 105:1039–1045 (Sep. 1987).

Sporn et al., "Transforming Growth Factor–β: Biological Function and Chemical Structure" *Science* 233:532–534 (Aug. 1, 1986).

ten Dijke et al., "Identification of another member of the transforming growth factor type β gene family" *Proc. Natl. Acad. Sci. USA* 85:4715–4719 (Jul. 1988).

Chao et al J Clin Invest 90 1786–1793 (1992).

Racke et al J Immunol 146 3012–3017 (1991).

Kururilla et al PNAS 88 2918–2921 (1991).

Flanders et al., *Development*, vol. 113, pp. 183–191, 1991.

Foster et al., *J. Neurosci*, vol. 8, pp. 4745–4754, 1988.

\* cited by examiner

FIG. 1a

Control (n=5)

FIG. 1b

FIG. 1c 72 (n=4)    120 (n=4)
hrs after 15 min hypoxia-ischemia
(moderate model)

FIG. 1f 5 (n=2)    72 (n=2)    120 (n=2)
hrs after 90 min hypoxia-ischemia (severe model)

TGF-β1 TO IMPROVE NEURAL OUTCOME

This application is a 371 of PCT/US92/09974, filed Nov. 20, 1992.

FIELD OF THE INVENTION

This invention relates to methods and pharmaceutical compositions for the treatment or prevention of central nervous system (CNS) damage and relates particularly to methods of treatment comprising increasing the concentration of transforming growth factor beta 1 (TGF-β1) and/or analogues thereof in the central nervous system of the patient to treat an injury or disease that causes damage to cells of the CNS.

BACKGROUND OF THE INVENTION

After asphyxial, traumatic, toxic, infectious, degenerative, metabolic, ischemic or hypoxic insults to the central nervous system (CNS) of man a certain degree of neural damage may result. For example, such neural damage can occur in cases of perinatal asphyxia associated with intrapartum fetal distress such as following abruption, cord occlusion or associated with intrauterine growth retardation; perinatal asphyxia associated with failure of adequate resuscitation or apnea; severe neural insults associated with near miss drowning, carbon monoxide inhalation, ammonia of other gaseous intoxication, cardiac arrest, collapse, coma, meningitis, hypoglycemia, or status epilepticus; episodes of cerebral asphyxia associated with coronary bypass surgery; cerebral anoxia or ischemia associated with stroke, hypotensive episodes, hypertensive crises; cerebral trauma; or cerebral degenerative diseases such as Alzheimers disease and multiple sclerosis.

Such neural damage can involve several different cell types of the CNS. For example, periventricular leucomalacia, a lesion which affects the periventricular oligodendrocytes is generally considered to be a consequence of hypoxicischemic injury to the developing preterm brain. Bejar, et al., *Am. J. Obstet. Gynecol.,* 159:357–363 (1988); Sinha, et al., *Arch. Dis. Child.,* 65:1017–1020 (1990); Young, et al., *Ann. Neurol.,* 12:445–448 (1982). Further cholinergic neuronal cell bodies are absent from most regions of the cortex in primates (Mesulam, et al., *Neurosci.,* 12:669–686 (1984)) and rats (Brownstein, et al., in *Handbook of Chemical Neuroanatomy, Classical Transmitters in the CNS,* pp. 23–53 (Elsevier, 1984)). Damage to the cerebral cortex by trauma, asphyxia, ischemia, toxins or infection is frequent and may cause sensory, motor or cognitive deficits. Glial cells which are non-neuronal cells in the CNS are necessary for normal CNS function. Infarcts are a principle component of hypoxic-ischemia induced injury and loss of glial cells is an essential component of infarction. Multiple sclerosis is associated with loss of myelin and oligodendrocytes, similarly Parkinson's disease is associated with loss of dopaminergic neurons.

Several growth factors have been reported to be induced after transient hypoxic-ischemia in the brain. After postasphyxial seizures, the proto-oncogene c-fos is induced in surviving neurons and in glial cells from infarcted regions. Gunn, et al., *Brain Res.,* S31:105–116 (1991). Nerve growth factor (NGF) synthesis is increased after hypoxia or seizures in the hippocampus and cerebral cortex. Lorez, et al., *Neurosci. Lett.,* 98:339–344 (1989); Gall, et al., *Science,* 245:758–761 (1989). However, little is known of the role of cytokines in brain injury. Glial cells have been shown to produce a number of cytokines including interleukin 3 (IL-3) and interleukin 6 (IL-6). Interleukin 1 (IL-1) has been reported to be elevated in cerebrospinal fluid after head injury in humans. McClain, et al., *J. Lab. Clin. Med.,* 110:48–54 (1987).

Transforming growth factor beta (TGF-β) is another example of a cytokine and is a multifunctional polypeptide implicated in the regulation of cellular or tissue response to injury or stress. For a general review of TGF-β and its actions, see Sporn, et al., *Science,* 233:532–534 (1986); Sporn et al., *J. Cell Biol.,* 105:1039–1045 (1987); Sporn, et al., *Nature,* 3232:217–219 (1988); and Sporn, et al, in *Peptide Growth Factors and Their Receptors I,* pp.419–472 (Springer-Verlag, 1990). TGF-β is found in various mammalian tissues, such as bone, platelets, and placenta, and methods for purifying the polypeptide from such natural sources, as well as for producing it in recombinant cell culture, have been described. See, for example, Assoian, et al., *J. Biol. Chem.,* 258:7155–7160 (1983); Frolik, et al., *Proc. Nat. Acad. Sci.,* 80:3676–3680 (1983); Heimark, et al., *Science,* 233:1078–1080 (1986); Sporn, et al., U.S. Pat. No. 5,104,977; Derynck, et al., *Nature,* 316:701–705 (1985); Derynck, et al., U.S. Pat. No. 4,886,747.

There are several molecular forms of TGF-β, including those forms which are commonly referred to as TGF-β1 (Derynck, et al., *Nature,* 316:701–705 (1985)), TGF-β2 (deMartin, et al., *EMBO J.,* 3673–3677 (1987); Madison, et al., *DNA,* 7:1–8 (1988)), TGF-β3 (Jakowlew, et al., *Mol. Endocrin.,* 2:747–755 (1988); Ten Dijke, et al., *Proc. Nat. Acad. Sci.,* 85:4715–4719 (1988); Derynck, et al., *EMBO J.,* 7:3737–3743 (1988)), TGF-β4 (Jakowlew, et al., *Mol. Endocrin.,* 2:1186–1195 (1988), and TGF-β5 (Kondaiah, et al., *J. Biol. Chem.,* 265:1089–1093 (1990).

It is an object of the invention to provide methods and pharmaceutical compositions for treating or preventing CNS injury or damage. The invention is based upon the inventors' successful research into the role and effects of TGF-β in the CNS.

SUMMARY OF THE INVENTION

Accordingly, in a first aspect the invention consists in a method of treating neural damage suffered after a CNS insult characterized in that it comprises the step of increasing the active concentration(s) of TGF-β1 and/or analogues of TGF-β1 (such as other molecular forms of TGF-β) in the CNS of the patient. Preferably, the concentration of TGF-β1 in the CNS of the patient is increased.

The term "treat" when used herein refers to the effecting of a reduction in the severity of the CNS damage, by reducing infarction, and loss of glial cells, non-cholinergic neuronal cells, or other neuronal cells, suffered after a CNS insult. It encompasses the minimizing of such damage following a CNS insult.

Preferably, TGF-β1 and/or analogues thereof are administered to the patient directly. Alternatively, a compound may be administered which upon administration to the patient, increases the active concentration of TGF-β1 or naturally occurring analogues of TGF-β1 in the CNS of the patient. For example, positively regulating binding proteins of TGF-β1, or naturally occurring analogues thereof may be administered.

Preferably, the pharmaceutical compositions described herein are administered in the period from the time of injury to 100 hours after the CNS insult and more preferably 0.5 to 8 hours after the CNS insult.

In one embodiment of the invention, said TGF-β1 and/or an analogue or analogues thereof is administered by lateral cerebro ventricular injection into the brain of a patient in the inclusive period from the time of the CNS insult to 8 hours thereafter.

In another embodiment, TGF-β1 and/or an analogue or analogues thereof is administered through a surgically inserted shunt into the cerebro ventricle of a patient in the inclusive period from the time of the CNS insult to 8 hours thereafter.

In yet another embodiment, TGF-β1 and/or an analogue or analogues thereof is administered peripherally into a patient for passage into the lateral ventricle of the brain in the inclusive period of from the time of the CNS insult to 8 hours thereafter.

Preferably, it is TGF-β1, itself, that is administered by way of lateral cerebro ventricle injection or by use of the surgically inserted shunt.

Preferably the pharmaceutical compositions are administered according to the pattern of injury or time lapsed after a CNS insult.

Preferably the dosage range administered is from about 0.0001 to 100 μg of TGF-β1 or said analogue or said compound that elevates the concentration thereof per 100 grams of body weight.

TGF-β1 may be used alone or in conjunction with other therapeutic agents, including other growth factors designed to ameliorate against loss of CNS cells such as glia and non-cholinergic neurons.

By "prevent" is meant a reduction in the severity of CNS damage suffered after a CNS insult and may also include inhibition of the symptoms of CNS damage.

In yet a further aspect, the invention relates to the use of TGF-β1 and/or analogues thereof in the preparation of pharmaceutical compositions for treating CNS damage.

Additionally, the invention comprises the use of a compound which, upon administration to a patient, increases the active concentration of TGF-β1 and/or naturally occurring analogues thereof in the CNS of the patient in the preparation of pharmaceutical compositions for treating injury to the CNS.

The invention also provides pharmaceutical compositions suitable for treating CNS damage suffered after a CNS insult comprising TGF-β1, and/or analogues thereof optionally provided in a pharmaceutically acceptable carrier or diluent.

The pharmaceutical composition for treating CNS damage may also comprise a compound which, upon administration to the patient suffering CNS damage, increases the active concentration of IGF-1 and/or naturally occurring analogues thereof in the CNS of said patient.

DESCRIPTION OF THE PREFERRED EMBODIMENTS

The invention relates to a method of treating CNS damage suffered after a neural insult. For example, the patient may have suffered perinatal asphyxia or cerebral asphyxia or ischemia associated with a stroke or other non-limiting examples of neural insults having been described earlier herein. In these instances, it is desirable to reduce or eliminate the symptoms of neural damage.

CNS damage may for example be measured by the degree of permanent neural deficit cognitive function, and/or propensity to seizure disorders.

It is desirable that the concentration of TGF-β1 and/or analogues thereof in the central nervous system and in the brain of the patient in particular should be increased in order to treat the neural damage. Accordingly, TGF-β1 and/or analogues thereof can be administered directly to the patient. By TGF-β1 is meant transforming growth factor beta-1. By "analogues" (or "biologically active analogues") of TGF-β1 is meant compounds which exert a similar biological effect to TGF-β1 and includes naturally occurring analogues (eg. TGF-β2, TGF-β3, TGF-β4, TGF-β5) or any of the known synthetic analogues of TGF-β1. These compounds can be derived from humans or other animals. TGF-β1 and analogues can be purified from natural sources or produced by recombinant DNA techniques.

Alternatively, compounds can be administered which, upon administration to the patient, increase the active concentration of TGF-β1 and/or naturally occurring analogues thereof in the central nervous system. By "active concentration" is meant the biological concentration of TGF-β1 and/or analogues in the central nervous system of the patient able to exert an effect on neural damage.

TGF-β1, its analogues, and compounds which elevate the active concentrations thereof can be administered centrally or systematically. Desirably the compositions are administered directly to the CNS of the patient and in particular to the region where the greatest damage has occurred. Accordingly, the compositions are administered directly into the brain or cerebrospinal fluid by techniques including lateral ventricular through a burrhole or anterior fontanelle, lumbar or cisternal puncture or the like. The compositions also are administered by intravenous, intra-cerobrospinal, intrathecal, or intrasynovial routes. In addition, they may be administered with other agents or growth factors, for example, insulin-like growth factor-1 (IGF-1).

For the prevention or treatment of CNS injury, the appropriate dosage of TGF-β1 or one of its analogues or a compound capable of elevating the physiological concentrations of TGF-β1, will depend on the type of injury to be treated, as defined above, the severity and course of the injury, whether such TGF-β1 compositions are administered for preventive or therapeutic purposes, previous therapy, the patient's clinical history and response to the TGF-β1 compositions, and the discretion of the attending physician. The TGF-β1 compositions are suitably administered to the patient at one time or over a series of treatments.

The foregoing examples show that the expression of TGF-β1 after a neural insult follows a specified time course and occurs in specified areas of the body. Accordingly, the compositions should be administered according to the pattern of CNS damage and time lapsed subsequent to an insult so as to produce the most desirable results.

The compositions may for example be administered about 0.5 to 100 hours after an insult. Alternatively, the composition may be administered prior to a potential CNS insult (e.g. prior to cardiac bypass surgery) so as to prevent or reduce the degree of neural damage suffered after insult.

A suitable dosage range may for example be between about 0.0001 to 100 μg of TGF-β1 and/or analogues or compounds that elevate the concentration thereof per 100 gm of body weight where the composition is administered centrally.

The invention also provides pharmaceutical compositions for treating neural damage suffered after an insult. The pharmaceutical compositions comprise TGF-β1 and/or analogues thereof or a compound which elevates the concentration of TGF-β1 in the CNS. TGF-β1, its analogues, and compounds that elevate the concentration thereof can be manufactured by recombinant DNA techniques such as those described in U.S. Pat. No. 4,886,747. Alternatively, such substances an be isolated from natural sources. Optionally, such pharmaceutical compositions are provided in a pharmaceutically acceptable carrier or diluent that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, polysaccharides such as cellulose or methylcellulose, potassium hydrogen phosphate, sodium chloride, zinc salts, colloidal silica, magnesium trisilicate, polyvinyl pyrrolidone, and polyethylene glycol. Suitable diluents include sterile aqueous solutions comprising one or more of such carriers. TGF-β1 is typically formulated at an acidic pH at which it is biologically active The invention is supported by the following experimental data. In the studies described in the following Examples, it was found that:

1) TGF-β1 mRNA is expressed after a neural insult over a defined time course in specific regions of injury and TGF-β1 itself can be detected by immunocytochemistry.
2) Alterations in central nervous system levels of TGF-β1 can alter neural outcome resulting as a consequence of a standardized neural insult.
3) Lower doses of TGF-β1 improve its efficacy in treating neural damage.

These Examples, however, are offered by way of illustration only, and are not intended to limit the invention in any manner. All patent and literature references cited throughout the specification are expressly incorporated.

EXAMPLE 1

The objective of this study was to study the expression of TGF-β1 in the central nervous system after a neural insult.

Twenty one day old rats were subjected to unilateral carotid ligation followed by inhalational asphyxia under defined conditions to produce either mild or severe neuronal loss on the ligated side.

Mild or severe neuronal loss was induced in 21 day rates as follows: The right carotid artery was ligated under light halothane anaesthesia. They were then placed in an incubator at 34° C. and 85% humidity. The inspired gases were replaced by 8% $O_2$ in nitrogen for 15 minutes (mild) or 90 minutes (severe) then returned to air. At various times after hypoxia (1 hour, 5 hours, 3 and 5 days) the animals were anaesthetized with pentobarbitone (Nembutal), the brains removed and snap frozen on dry ice for in situ hybridization. For histology, rats were sacrificed 5 days after hypoxia and then perfused with 0.9% saline followed by formaldehydeacetic acid-methanol (1:1:8).

At defined times after the asphyxia the rats were sacrificed for histology. After 90 minutes asphyxia (severe) neuronal loss was assessed by thionine/acid fuchsin stain was widespread within the ligated cortex. There was severe loss of neurons in the middle cerebral artery territory, including the lateral cortex, hippocampus, striatum and thalamus. In situ hybridization histochemistry was performed using a TGF-β1 cDNA probe comprising nearly the entire coding sequence of TGF-β1, provided by Dr. R. Derynck. Hybridization histochemistry was performed essentially as described in McCabe, et al., *J. Histochem, Cytochem.*, 34:45–50 (1986) and in Smith, et al., *Ann. Neurophathol.*, 64:319–332 (1984).

After hybridization, the sections were washed 4 times in 2xSSC plus 10 mM β. mercaptoethanol at room temperature for 10 minutes each, 4 times in 2xSSC at room temperature for 10 minutes each, twice in 2xSSC at 50° C. for 10 minutes each.

Controls were performed using RNAase A (40 μg/ml 0.5M NaCl/20 mM Tris, pH 7.5/1 mM EDTA at 37° C.). RNAase pretreatment almost entirely depressed the signal Northern blots on each probe revealed the anticipated major band at 2.5 kb.

The resulting signal for TGF-β1 mRNA as measured by in situ hybridization showed an induction of the TGF-β1 mRNA restricted to the areas of neuronal damage. Following mild asphyxia (15 minutes), induction of TGF-β1 mRNA was observed in the ligated brain in layer 3 of the cerebral cortex, the dentate gyrus, CA1 and CA2 regions of the pyramidal layer of the hippocampus.

Following severe asphyxia (90 minutes), TGF-β1 mRNA was detectable by one hour post insult in the hippocampal dentate gyrus, CA 1 and CA 2 regions, and choroid plexus. By 5 hours it was detectable in the cortex and striatum on the ligated side. By 72 hours marked expression was observed throughout the whole cerebral and puriform cortex, striatum, thalamus and hippocampus of the ligated side but no expression was observed on the non-ligated side in which no neuronal death was observed (FIG. 1).

The specificity of the induction was demonstrated by predominately unilateral expression on the ligated side, lesser induction in animals subjected to a lesser insult and by negative controls using RNAase A. The probe was also used to hybridize a Northern blot of rat liver poly(A) RNA samples. The bands after hybridization to the TGF-β1 probe are in agreement with the data reported in the literature.

Immunohistochemistry was performed using anti-H rabbit TGF-β1 polyclonal anti-serum. Cells staining for TGF-β1 could be identified in the damaged region of the ligated hemisphere. This staining was seen in cells with macrophage-like appearance.

The data suggests that following an hypoxic ischemic insult, TGF-β1 is induced in macrophages, particularly in the area of damage.

EXAMPLE 2

The objective of this study was to assess the effect of administering TGF-β1 after a neural insult.

Adult rats (250–350 grams) were used. The experiment involved treating the rats with TGF-β1 after a neural insult. These rats had an hypoxic-ischemic insult to one cerebral hemisphere induced in a standard manner. One carotid artery was ligated and the animal was subjected two hours later to a defined period of inhalational hypoxia. The degree, length of hypoxia, ambient temperature and humidity were defined to standardize the degree of damage. The conditions were inhaled oxygen (6%), 10 minutes of hypoxia at ambient temperature of 31° and 85% humidity. The animals were maintained in an incubator for one hour then returned to their standard cages. They were sacrificed five days later for histological analysis using stains (acid-fuchsin) specific for necrotic neurons.

In such experiments typical neuronal death is restricted to the side of the side of arterial ligation and is primarily in the hippocampus, dentate gyrus and lateral cortex of the ligated hemisphere.

Unilateral hypoxic-ischemic injury was induced in adult (300±10 g) male Wister rats. The rats underwent unilateral carotid ligation under light halothane anaesthesia. Following one hour recovery they were placed in an incubator at 31° C. and 85±5% humidity for one hour before insult. They were subject to 10 minutes inhalational asphyxia (FiO2 6.0%) and maintained in the incubator for one hour after asphyxia. Two hours after the termination of the inhalational insult, a single stereotaxically controlled lateral cerebroventricular injection of either 0.05 μg recombinant TGF-β1 or artificial cerebrospinal fluid (CSF) was given.

Recombinant TGF-β1 or diluent was prepared and administered to weight-matched pairs as follows: Two hours after asphyxia the rats were given a light halothane anaesthetic, and a single ICV injection of either 20 μl of CSF (n-6) or 20 μl of CSF plus 0.05 μg TGF-β1 (n-6) was given. Recombinant TGF-β1 (Genentech, Inc., South San Francisco, Calif. 94080 USA) was dissolved in the CSF diluent at 2.5 μgl/ml. This solution was diluted 9 times with 0.15M PBS (phosphate buffered saline) giving a pH of 7.0.

The animals were then maintained for 120 hours, anaesthetized and the brains fixed in situ with formaldehyde-acetic acid-methanol (1:1:8) for histological assessment.

Surviving and dead neurons were discriminate with the use of an thionin/acid fuschin staining technique. Williams, et al., *Ped. Res.*, 27:561–565 (1990); Brown, et al., *J. Neurol. Sci.*, 16:59–84 (1971).

The degree of neural damage suffered was quantified by measuring the neuronal loss score. The neuronal loss scores are the average from the susceptible regions of the hippocampus and cerebral cortex (100% equals total loss of neurons, 0% equals 0 loss).

The percentage of dead neurons was estimated by two independent observers, one of whom was blinded to the experiment. The correlation between scores obtained by the two observers was r-0.92 p,0.0001. The effect of treatment was evaluated with MANOVA followed by pair wise comparisons of each region using Fisher's least-significant-difference procedure.

Figure 1A:
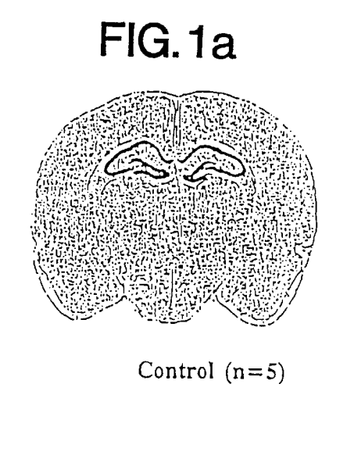
FIG. 1a shows a composite drawing illustrating the distribution of TGF-β1 mRNA in control animals for Example 1.
Figure 1B:
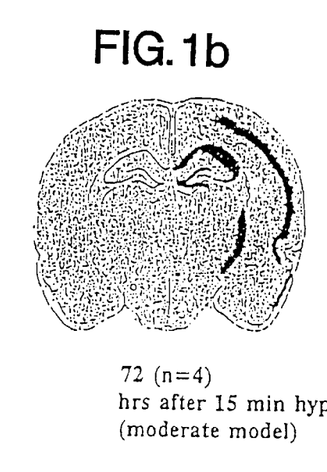
FIG. 1b shows a composite drawing illustrating the distribution of TGF-β1 mRNA 72 hours after 15 minute hypoxia-ischemia as described in Example 1.
Figure 1C:
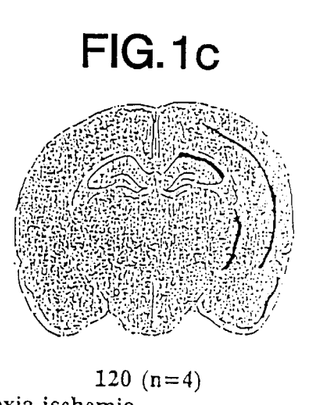
FIG. 1c shows a composite drawing illustrating the distribution of TGF-β1 mRNA 120 hours after 15 minute hypoxia-ischemia as described in Example 1.
Figure 1D:
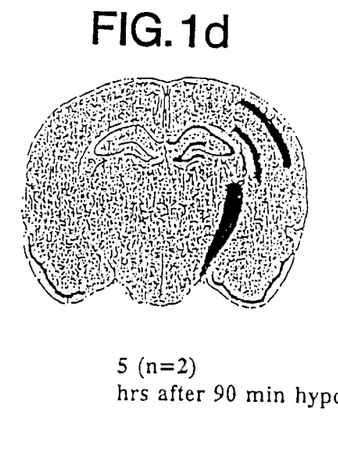
FIG. 1d shows a composite drawing illustrating the distribution of TGF-β1 mRNA 5 hours after 90 minute hypoxia-ischemia as described in Example 1.
Figure 1E:
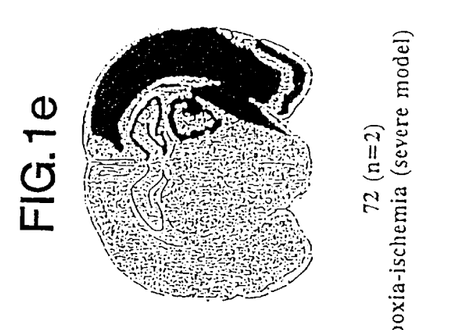
FIG. 1e shows a composite drawing illustrating the distribution of TGF-β1 mRNA 72 hours after 90 minute hypoxia-ischemia as described in Example 1.
Figure 1F:
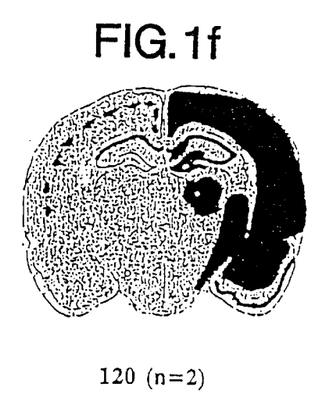
FIG. 1f shows a composite drawing illustrating the distribution of TGF-β1 mRNA 120 hours after 90 minute hypoxia-ischemia as described in Example 1.
Figure 2:
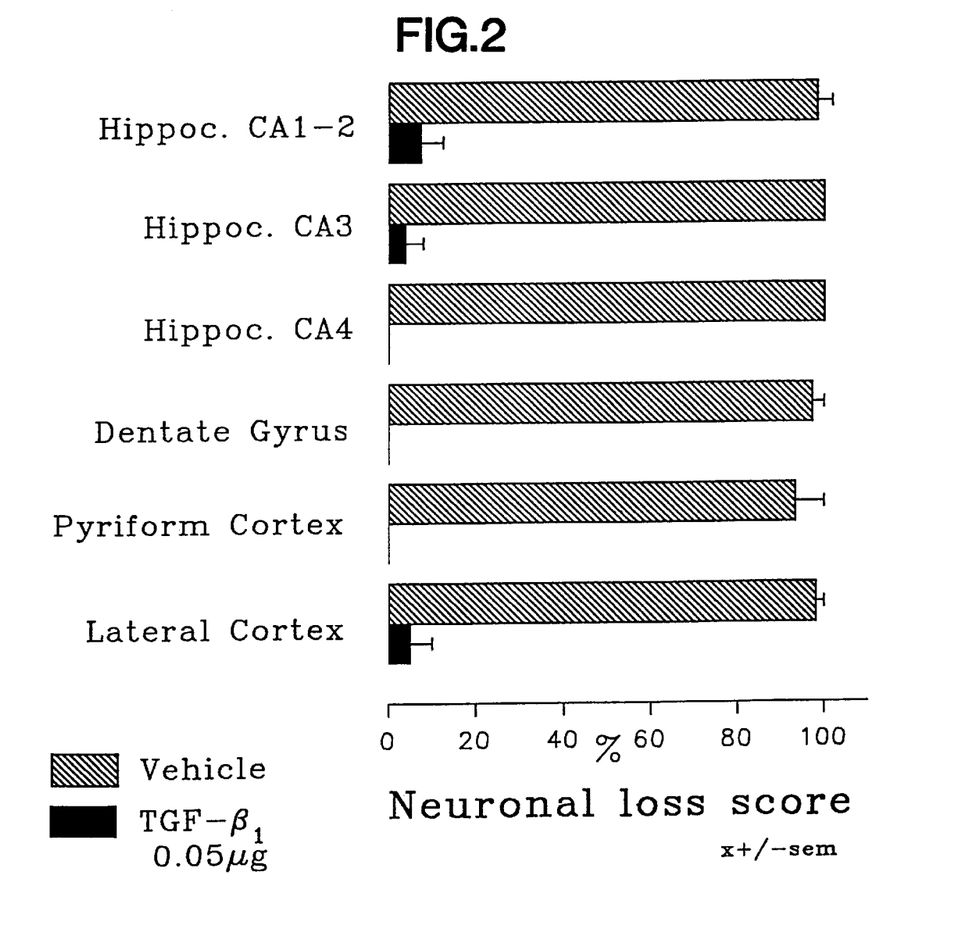
FIG. 2 is a histogram illustrating the neuronal loss for TGF-β1 treated and control rats in Example 2.

The results are shown in FIG. 2. TGF-β1 therapy reduced the extent of neuronal death in the ligated hemisphere compared to the CSF-treated controls (p<0.01). A single central injection of TGF-β1 following an asphyxial insult in the adult rat was associated with a marked improvement in outcome as assessed histologically (See Table 1).

TABLE 1

Effect of TGF-β1 treatment on percent neuronal loss following hypoxic-ischemic injury (6 groups; mean ± sem).

| Region | % Neuronal less upon treatment with | |
| --- | --- | --- |
| (0.05 μg) | CSF (control) | TGF-β1 |
| Hippocampal CA1-2 | 98.4 ± 4 | 7.6 ± 5 |
| Hippocampal CA3 | 100.0 | 4.0 ± 4 |
| Hippocampal CA4 | 100.00 | 0.0 |
| Dentate gyrus | 97.2 ± 3 | 0.0 |
| Pyriform cortex | 93.2 ± 7 | 0.0 |
| Lateral cortex | 98.0 ± 2 | 5.0 ± 5 |

EXAMPLE 3

The objective of this study was to confirm the observations of Example 2 and establish the most effective dosage range.

The experiment was the same to the of Example 2 except that two further groups were treated with higher doses of TGF-β1.

Hypoxic-ischemic insult was induced in rats as discussed for Example 2. Rats (n-6 for each treatment) were administered either CSF, CSF+0.05 μg TGF-β1, CSF+0.5 μg TGF-β1 or CSF+5 μg TGF-β1 two hours after the inhalational insult. Rats (n-1) from each treatment were treated simultaneously. The same techniques for measuring the degree of insult at those discussed for Example 2 where employed.

Figure 3:
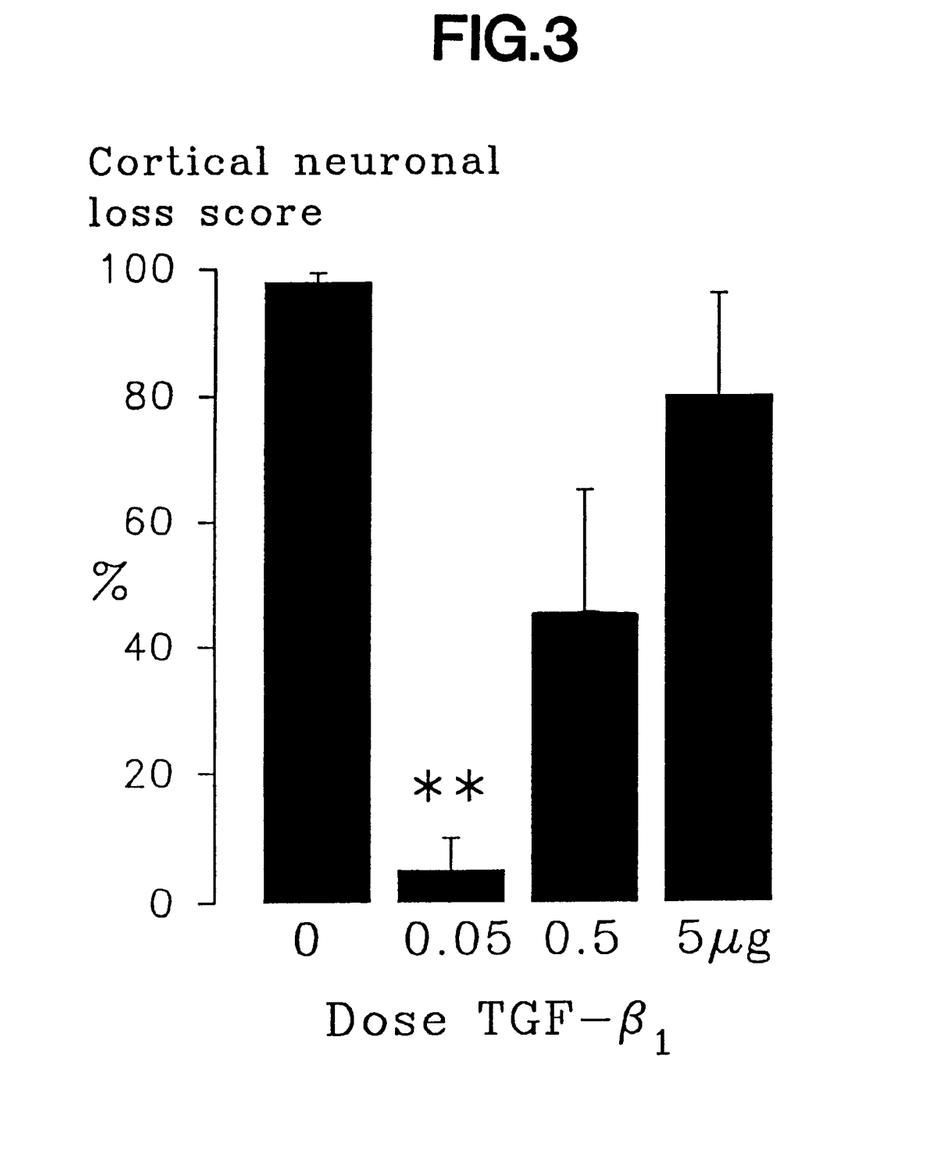
FIG. 3 is a histogram illustrating the neuronal loss for TGF-β1 treated and control rats in Example 3.

The results are shown in FIG. 3. As can be seen, 5 μg TGF-β1 had no significant effect on neuronal loss. On the other hand, 0.5 μg TGF-β1 reduced (p<0.05) neuronal loss in the cerebral cortex but 0.05 μg TGF-β1 was significantly (p<0.05) more effective. Similar effects were seen in other neuronal areas. Further experiments have shown that dosages in the range of about 0.01 μg to 0.05 μg are most effective.

DISCUSSION

The results of the experiments described above were statistically highly significant. In Examples 2 and 3, where TGF-β1 was given post-asphyxia, TGF-β1 therapy at doses less than 0.5 μg/rat or lower markedly improved outcome compared to CSF treated controls. We therefore conclude that therapeutic elevation of TGF-β1 in the cerebral spinal fluid either directly or indirectly after an insult is advantageous to outcome. The results in Example 3 further show that the greatest efficacy is seen at low doses of TGF-β1.

The present invention, therefore, recognizes the role of an administration of TGF-β1 and/or other compounds of similar effect into a patient prior to, simultaneous with, or following a CNS insult with the consequential result that CNS damage is minimized by preventing the otherwise consequential damage that otherwise would occur following the injury. The invention provides methods and pharmaceutical compositions for treating or for preventing neural damage. Neural damage may be associated with asphyxia, hypoxia, toxins, ischemia or trauma. Although it will be appreciated that the main application of the invention is to humans, the usefulness of the invention is not limited thereto and treatment of non-human animals (especially mammals) is also within the scope of the invention.

What is claimed is:

1. A method of treating central nervous system injury in a mammal, comprising administering to the central nervous system of said mammal TGF-β1 in the period from the time of the central nervous system injury to about 8 hours after said injury and wherein TGF-β1 is administered to said mammal in an amount from about 0.0033 to about 0.15 μg of TGF-β1 per 100 gm of body weight of said mammal wherein said administration results in a reduction in the severity of central nervous system damage, wherein the central nervous system injury affects non-cholinergic neuronal cells.

2. A method of treating central nervous system injury in a mammal, comprising administering to the central nervous system of said mammal TGF-β1 in the period from the time of the central nervous system injury to about 8 hours after said injury and wherein TGF-β1 is administered to said mammal in an amount from about 0.0033 to about 0.15 μg of TGF-β1 per 100 gm of body weight of said mammal wherein said administration results in a reduction in the severity of central nervous system damage, wherein the central nervous system injury affects glial cells.

3. A method of treating central nervous system injury in a mammal, comprising administering to the central nervous system of said mammal TGF-β1 in the period from the time of the central nervous system injury to about 8 hours after said injury and wherein TGF-β1 is administered to said mammal in an amount from about 0.0033 to about 0.15 μg of TGF-β1 per 100 gm of body weight of said mammal wherein said administration results in a reduction in the severity of central nervous system damage, wherein the central nervous system injury is a consequence of Parkinson's disease.

4. A method of treating central nervous system injury in a mammal, comprising administering to the central nervous system of said mammal TGF-β1 in the period from the time of the central nervous system injury to about 8 hours after said injury and wherein TGF-β1 is administered to said mammal in an amount from about 0.0033 to about 0.15 μg of TGF-β1 per 100 gm of body weight of said mammal wherein said administration results in a reduction in the severity of central nervous system damage, wherein the central nervous system injury is a consequence of multiple sclerosis.

5. A method of treating central nervous system injury in a mammal, comprising administering to the central nervous system of said mammal TGF-β1 in the period from the time of the central nervous system injury to about 8 hours after said injury and wherein TGF-β1 is administered to said mammal in an amount from about 0.0033 to about 0.15 μg of TGF-β1 per 100 gm of body weight of said mammal wherein said administration results in a reduction in the severity of central nervous system damage, wherein the central nervous system injury is a consequence of a demyelinating disorder.

6. A method of treating central nervous system injury in a mammal, comprising administering to the central nervous system of said mammal TGF-β1 in the period from the time of the central nervous system injury to about 8 hours after said injury and wherein TGF-β1 is administered to said mammal in an amount from about 0.0033 to about 0.15 μg of TGF-β1 per 100 gm of body weight of said mammal wherein said administration results in a reduction in the severity of central nervous system damage, wherein the TGF-β1 is administered peripherally into the mammal for passage into the lateral ventricle of the brain.

* * * * *

UNITED STATES PATENT AND TRADEMARK OFFICE
CERTIFICATE OF CORRECTION

PATENT NO. : 6,204,240 B1
APPLICATION NO. : 08/232118
DATED : March 20, 2001
INVENTOR(S) : Gluckman et al.

It is certified that error appears in the above-identified patent and that said Letters Patent is hereby corrected as shown below:

Col. 8, Line 1 Claim 1. "A method of treating...in an amount from about 0.0033 to about 0.15 $\mu$g of TGF-$\beta$1 per 100 gm of body weight...injury afffects non-cholinergic neuronal cells." should read --"A method of treating...in an amount from about 0.0033 to about 0.0167 $\mu$g of TGF-$\beta$1 per 100 gm of body weight...injury afffects non-cholinergic neuronal cells."--

Col. 9, Line 10 Claim 2. "A method of treating...in an amount from about 0.0033 to about 0.15 $\mu$g of TGF-$\beta$1 per 100 gm of body weight...injury affects glial cells." should read --"A method of treating....in an amount from about 0.0033 to about 0.0167 $\mu$g of TGF-$\beta$1 per 100 gm of body weight...injury affects glial cells."--

Col. 9, Line 20 Claim 3. "A method of treating...in an amount from about 0.0033 to about 0.15 $\mu$g of TGF-$\beta$1 per 100 gm of body weight...injury is a consequence of Parkinson's disease." should read --"A method of treating...in an amount from about 0.0033 to about 0.0167 $\mu$g of TGF-$\beta$1 per 100 gm of body weight...injury is a consequence of Parkinson's disease."--

Col. 9, Line 31 Claim 4. "A method of treating...in an amount from about 0.0033 to about 0.15 $\mu$g of TGF-$\beta$1 per 100 gm of body weight...injury is a consequence of multiple sclerosis." should read --"A method of treating...in an amount from about 0.0033 to about 0.0167 $\mu$g of TGF-$\beta$1 per 100 gm of body weight... injury is a consequence of multiple sclerosis."--

Col. 10, Line 9 Claim 5. "A method of treating...in an amount from about 0.0033 to about 0.15 $\mu$g of TGF-$\beta$1 per 100 gm of body weight...injury is a consequence of a demyelinating disorder." should read --"A method of treating...in an amount from about 0.0033 to about 0.0167 $\mu$g of TGF-$\beta$1 per 100 gm of body weight... injury is a consequence of a demyelinating disorder."--

UNITED STATES PATENT AND TRADEMARK OFFICE
CERTIFICATE OF CORRECTION

PATENT NO. : 6,204,240 B1
APPLICATION NO. : 08/232118
DATED : March 20, 2001
INVENTOR(S) : Gluckman et al.

It is certified that error appears in the above-identified patent and that said Letters Patent is hereby corrected as shown below:

Col. 10, Line 21 Claim 6. "A method of treating...in an amount from about 0.0033 about 0.15 $\mu$g of TGF-$\beta$1 per 100 gm of body weight...for passage into the lateral ventricle of the brain." should read --"A method of treating...in an amount from about 0.0033 to about 0.0167 $\mu$g of TGF-$\beta$1 per 100 gm of body weight...for passage into the lateral ventricle of the brain."--

Signed and Sealed this

Seventeenth Day of July, 2007

JON W. DUDAS
*Director of the United States Patent and Trademark Office*